United States Patent [19]

Kato et al.

[11] Patent Number: 4,469,810

[45] Date of Patent: Sep. 4, 1984

[54] PROCESS FOR THE CALCINATION OF PHOSPHORUS-MOLYBDENUM CATALYST

[75] Inventors: Masaaki Kato, Hatsukaichi; Masatake Kamogawa, Otake; Toshiharu Nakano, Otake; Junji Furuse, Otake, all of Japan

[73] Assignee: Mitsubishi Rayon Company Limited, Tokyo, Japan

[21] Appl. No.: 457,220

[22] Filed: Jan. 11, 1983

[51] Int. Cl.$^3$ .............................................. B01J 27/14
[52] U.S. Cl. .................................. 502/209; 502/210; 502/211
[58] Field of Search ................................ 252/435, 437

[56] References Cited

U.S. PATENT DOCUMENTS

| | | | |
|---|---|---|---|
| 4,163,862 | 8/1979 | Dolhyj et al. | 252/435 X |
| 4,190,556 | 2/1980 | Grasselli et al. | 252/435 X |
| 4,220,802 | 9/1980 | Okiyama et al. | 252/437 X |
| 4,260,822 | 4/1981 | Krieger et al. | 252/435 X |
| 4,338,463 | 7/1982 | Show et al. | 252/435 X |

FOREIGN PATENT DOCUMENTS

| | | | |
|---|---|---|---|
| 0000564 | 2/1979 | European Pat. Off. | 252/437 |
| 0057918 | 2/1982 | European Pat. Off. | 252/437 |
| 52-25716 | 2/1977 | Japan | 252/437 |

*Primary Examiner*—Delbert E. Gantz
*Assistant Examiner*—William G. Wright
*Attorney, Agent, or Firm*—Oblon, Fisher, Spivak, McClelland & Maier

[57] ABSTRACT

A process for improving the operating characteristics of a phosphorous-, molybdenum-, and oxygen-containing catalyst used for the production of an unsaturated carboxylic acid by gas phase catalytic oxidation of a corresponding unsaturated aldehyde, comprising the step of calcinating the catalyst at a temperature of 300°–500° C. while a gas containing 0.05–3 vol. % of ammonia and/or steam is passed over the catalyst.

7 Claims, 1 Drawing Figure

PROCESS FOR THE CALCINATION OF PHOSPHORUS-MOLYBDENUM CATALYST

BACKGROUND OF THE INVENTION

1. Field of the Invention

The present invention relates to a process for the calcination of a catalyst containing phosphorus, molybdenum and oxygen used for the production of an unsaturated acid by gas phase catalytic oxidation of the corresponding unsaturated aldehyde. More particularly, the present invention relates to a process for the calcination of a catalyst containing phosphorus, molybdenum and oxygen used for the production of acrylic acid or methacrylic acid by gas phase catalytic oxidation of acrolein or methacrolein.

2. Description of the Prior Art

Various catalysts have been proposed for the gas phase catalytic oxidation of acrolein or methacrolein. Among them, those containing phosphorus, molybdenum and oxygen have relatively excellent properties. Some of the present inventors proposed a catalyst containing phosphorus, molybdenum and oxygen in the specifications of Japanese Patent Publication Nos. 23013/75 and 23014/75. If such a catalyst is prepared under specific conditions, its activity and selectivity are improved remarkably over other prior art catalysts. However, the catalyst still has insufficient reproducibility of performance from batch to batch. As the scale of production is increased, the scattering of performance becomes higher. Thus, the catalyst has not always been satisfactory from an industrial viewpoint.

SUMMARY OF THE INVENTION

It is an object of the present invention to produce a catalyst suitable for the catalytic oxidation of an unsaturated aldehyde to the corresponding unsaturated acid.

It is a further object of the invention to provide a method of producing such a catalyst that is satisfactory from an industrial viewpoint.

It is yet another object of the invention to reproducibly produce a catalyst having high activity and selectivity.

These and other objects of the invention as will hereinafter become more readily apparent have been accomplished by providing a process for improving the operating characteristics of a phosphorus-, molybdenum-, and oxygen-containing catalyst used for the production of an unsaturated carboxylic acid by the gas phase catalytic oxidation of a corresponding unsaturated aldehyde, comprising the step of calcinating said catalyst at a temperature of 300°-500° C. while a gas containing 0.05-3% of ammonia or steam is passed over said catalyst.

DESCRIPTION OF THE PREFERRED EMBODIMENTS

Figure 1:
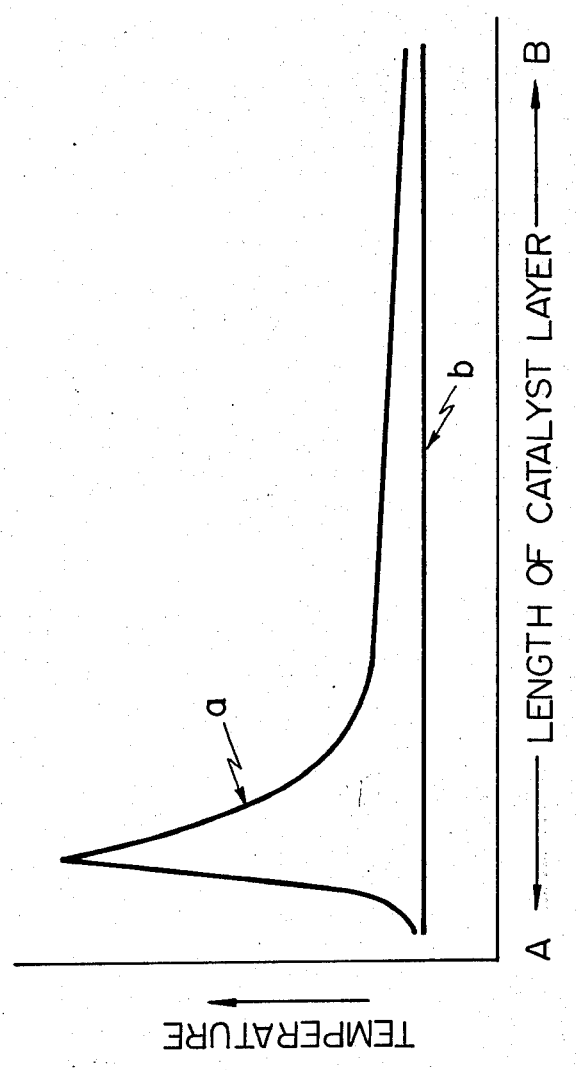

After intensive investigations of processes for producing the above-mentioned catalyst having a high performance and a high homogeneity, particularly on an industrial scale, the inventors have found that a catalyst having a high performance and a high homogeneity can be obtained by activating the catalyst composition during an otherwise known calcinating process at a temperature of 300°-500° C. for one to several ten hours while a gas containing ammonia or steam or both ammonia and steam in strictly controlled concentration is introduced into the calcinating system. The present invention has been completed on the basis of this finding.

The present invention provides a process for the calcination of a catalyst containing phosphorus, molybdenum and oxygen used for the production of acrylic acid or methacrylic acid by the gas phase catalytic oxidation of acrolein or methacrolein. The invention provides also a process for producing these and other unsaturated carboxylic acids in the presence of thus treated catalyst.

Catalysts containing phosphorus and molybdenum prepared by various processes in the prior art have activities as described above; i.e., the activities are variable. Particularly, the catalysts prepared by calcination in an air stream generally have an activity far higher than that of catalysts prepared by calcination without using an air stream. However, in the calcination of the catalyst, the activity of the catalyst becomes non-uniform as the amount of the catalyst being treated is increased and, therefore, the catalyst has non-uniform performance. Thus, the reproducibility of the catalyst is poor, and the calcination of the catalyst on an industrial scale is difficult. Under these circumstances, an improvement of the calcination process has eagerly been awaited.

After intensive investigations made for the purpose of elucidating the mechanism of the activation of catalysts containing phosphorus, molybdenum and oxygen by calcination and the causes of the non-uniform activity, the inventors have found the following facts: (1) When a catalyst is calcinated while a gas such as air is introduced into the system, the salts used as starting materials are decomposed and gaseous substances such as water vapor, ammonia, nitrogen oxides and the like are formed from the catalyst. (2) Therefore, the catalyst composition is exposed to a non-uniform gas atmosphere at various locations from the inlet to the outlet of the gas stream.

After further investigations made for the purpose of developing a process for the uniform calcination of the catalyst on the basis of these findings, the inventors have found that a catalyst having a high performance and a high homogeneity can be obtained by treating a catalyst composition obtained by an ordinary calcination process with a gas flow containing ammonia and/or steam in an amount controlled in the range of 0.05-3%.

The process of the present invention for the calcination of a catalyst may be employed for the calcination of catalysts containing phosphorus, molybdenum, oxygen and various other elements. Examples of other elements which may be contained in the catalysts include alkaline earth metals, arsenic, antimony, bismuth, copper, vanadium, tungsten, iron, manganese, tin, zirconium, cobalt, nickel, zinc, selenium, cadmium, niobium, tantalum, silicon, aluminum, titanium, rhodium, cerium, germanium, lead, chromium, thallium, indium, palladium, silver and tellurium. The catalyst may contain an ammonium ion. The starting material used for the preparation of the catalyst may be a hydroxide, oxide, salt, chloride or free acid. Examples of starting materials include phosphoric acid, molybdic acid, phosphomolybdic acid, ammonium molybdate, ammonium phosphomolybdate and moybdenum trioxide.

A typical example of the preparation process follows. An aqueous phosphoric acid solution is added to an aqueous ammonium molybdate solution. If necessary, a compound of another element, such as arsenic acid, copper nitrate or ammonium metavanadate, is added to the mixture, and the whole is evaporated to dryness under stirring. The resulting solid is further dried to remove residual water. The resulting cake is pulverized and then shaped into tablets, or diluted with a diluent and then shaped. Alternatively, the active agent may be carried on a suitable carrier. Thus-obtained catalyst may be calcined directly or after a heat treatment at a temperature of up to 340° C.

When an ammonia-containing gas is used in the process of the present invention, the ammonia concentration is 0.05–3%, preferably 0.05–1.5%. When a steam-containing gas or a gas containing both ammonia and steam is used, its concentration is in the range of 0.05–3%. If the concentration of ammonia and/or steam in the gas stream is below the above-mentioned ranges, the resulting catalyst has an insufficient effect and non-uniform activity. If the concentration is above the above-mentioned range, the catalyst obtained after the heat treatment has non-uniform activity and the activity realized is insufficient as a whole.

The calcination temperature is 300°–500° C., preferably 300°–420° C. The calcination time, which varies depending on the calcination temperature, atmosphere and concentration, is generally one to several tens of hours, particularly 1–30 hours.

The calcination process according to the present invention may be effected in an ordinarily used apparatus or furnace. According to the process of the present invention, it is possible to calcine a large amount of catalyst, since a catalyst having a high homogeneity can be obtained. For example, a catalyst charged in a reactor having a total length of 5–6 m can be treated. In this case, direction of the gas flow may be reversed in the course of the calcination. The temperature elevation rate until reaching the calcination temperature is 10°–200° C./h, particularly 10°–150° C./h. When the catalyst is calcined in a reactor and then an unsaturated acid is produced in the same reactor in the presence of the catalyst, it is preferred that the gaseous starting material to be reacted is fed in a direction opposite to the direction for the gas used for the calcination of the catalyst. A reason therefor is that the distribution of catalyst activity is slightly uneven for the inlet to the outlet of the calcination gas in some cases. In such a case, it is preferred for leveling the reacting amount to feed the starting gas, having a high unsaturated aldehyde concentration, in a catalyst part having a relatively low activity. As a matter of course, the unevenness of the activity distribution of the catalyst is negligible in many cases and, therefore, the flow direction of the gaseous starting material is not limited. The process wherein the catalyst is calcined in the reactor is preferred, since a catalyst having a high strength prior to the calcination can be charged into the reactor and, therefore, the pulverization of the catalyst can be prevented.

In the production of acrylic acid or methacrylic acid by the oxidation of acrolein or methacrolein in the presence of the catalyst activated by the process of the present invention, a starting gas comprising a mixture of acrolein or methacrolein and a gas containing molecular oxygen, such as air, is used. Steam, nitrogen, carbon dioxide or another inert gas may be introduced therein as a diluent. Particularly, the presence of steam exerts a favorable influence on the conversion of acrolein or methacrolein into acrylic acid or methacrylic acid as well as favorably influencing the selectivity of these reactions. The concentration of acrolein or methacrolein in the starting gas, which may be varied over a broad range, is preferably 1–20 vol. %, particularly 3–15 vol. %. The oxygen concentration is preferably 0.3–4 moles, particularly 0.4–3.2 moles per mole of acrolein or methacrolein. The reaction pressure ranges from atmospheric pressure to several atmospheres. The reaction temperature is 240°–390° C., particularly 270°–340° C. The gas space velocity, which varies depending on the reaction pressure and the reaction temperature, is preferably 300–10,000 h$^{-1}$.

The following examples, which are included herein for purposes of illustration only and are not intended to be limiting of the invention or any embodiment thereof, unless so specified, will further illustrate the process of the present invention. In the examples, parts are given by weight and the conversion and selectivity are calculated according to the following formulas:

Conversion (%) =

$$\frac{\text{(Mole number of acrolein or methacrolein reacted)}}{\text{(Mole number of acrolein or methacrolein fed)}} \times 100$$

Selectivity (%) =

$$\frac{\text{(Mole number of acrylic acid or methacrylic acid formed)}}{\text{(Mole number of acrolein or methacrolein reacted)}} \times 100$$

EXAMPLE 1

3,000 parts of ammonium paramolybdate were dissolved in 8,000 parts of pure water at 70° C. 163 parts of 85% phosphoric acid and 147 parts of 60% aqueous arsenic acid solution were added to the solution.

The liquid mixture was evaporated to dryness by heating the same under stirring. The residue was further dried by maintaining the same at 130° C. for about 16 h. The resulting cake was pulverized and molded.

660 parts of the moldings thus obtained were charged in a stainless steel pipe and having an inner diameter of 27.5 mm and a length of 1 m. The temperature was elevated to 380° C. at a rate of 80° C./h while 1000 l/h of air containing 0.06 vol. % of ammonia was introduced therein. They were kept at that temperature for 2 h and then heat-treated for an additional 4 h after reversing the flow direction. After cooling, the catalyst was taken out in portions to obtain substantially equal parts. They were classified as catalysts (1), (2), (3), (4) and (5) numbering from the inlet side of the initial gas flow. Each of the catalysts was charged in a reaction tube having an inner diameter of 16 mm. The furnace temperature was maintained at 280° C. A gaseous starting material having a composition comprising 5 vol. % of methacrolein, 47.8 vol. % of air, 20 vol. % of steam and 27.2 vol. % of nitrogen was introduced therein at a space velocity of 1,000 h$^{-1}$ to carry out the reaction.

The results are shown in the following table:

| Catalyst No. | Methacrolein conversion (%) | Methacrylic acid selectivity (%) |
|---|---|---|
| (1) | 72.3 | 84.8 |
| (2) | 72.0 | 85.0 |
| (3) | 70.1 | 85.7 |
| (4) | 70.5 | 85.4 |
| (5) | 71.9 | 85.2 |

Comparative Example 1

The same procedure as in Example 1 was repeated except that air containing 0.01% of ammonia was used as the gas used for the heat treatment during calcination.

| Catalyst No. | Methacrolein conversion (%) | Methacrylic acid selectivity (%) |
|---|---|---|
| (1) | 65.4 | 60.0 |
| (2) | 74.3 | 63.9 |
| (3) | 80.8 | 72.4 |
| (4) | 76.5 | 70.9 |
| (5) | 71.1 | 68.8 |

It can be seen from these results that if the ammonia content of the gas flow is too low during calcination, the distribution of activity and selectivity in the various parts of the catalyst become significant after the calcination of a large amount of the catalyst.

Comparative Example 2

The same procedure as in Example 1 was repeated except that air containing 5% of ammonia was used as the gas used for the heat treatment.

| Catalyst No. | Methacrolein conversion (%) | Methacrylic acid selectivity (%) |
|---|---|---|
| (1) | 27.7 | 72.4 |
| (2) | 30.6 | 74.1 |
| (3) | 35.9 | 75.6 |
| (4) | 29.8 | 72.3 |
| (5) | 25.0 | 70.3 |

It can be seen from these results that if the ammonia content of the gas flow is excessive during calcination, the catalyst activity is not as high as in the example of the invention and methacrylic acid selectivity is not increased.

EXAMPLE 2

3,000 parts of ammonium paramolybdate were dissolved in 14,000 parts of pure water at about 60° C. 41.3 parts of ammonium metavanadate were added therein to obtain a solution. Then, 163 parts of 85% phosphoric acid and 73.6 parts of germanium dioxide were successively added to the solution. A solution of 143 parts of potassium nitrate in 1,700 parts of pure water and a solution of 57.2 parts of ferric nitrate in 600 parts of pure water were added thereto, and the mixture was evaporated to dryness by heating the same under stirring. The residue was further dried at 130° C. for 16 h. The resulting cake was pulverized, mixed with a lubricant and molded.

The moldings were charged in a reaction tube having an inner diameter of 27.5 mm and a length of 3 m. The temperature was elevated to 385° C. at a rate of 25° C./h while 1,000 l/h of air containing 0.5% of steam was introduced therein. They were maintained at that temperature for 4 h and then treated for an addition 4 h after reversing the flow direction. After cooling, the catalyst was taken out in portions to obtain five substantially equal parts in the same manner as in Example 1. Each of them was charged in a reaction tube having an inner diameter of 22 mm. The reaction was carried out under the same reaction conditions as in Example 1 except that the reaction temperature was altered to 300° C. and amounts of methacrolein, air and steam were 4%, 60% and 36%, respectively.

| Catalyst No. | Methacrolein conversion (%) | Methacrylic acid selectivity (%) |
|---|---|---|
| (1) | 84.1 | 82.3 |
| (2) | 82.2 | 83.9 |
| (3) | 80.5 | 84.9 |
| (4) | 81.2 | 84.0 |
| (5) | 83.0 | 84.0 |

Comparative Example 3

The same procedure as in Example 2 was repeated except that the gas used for the heat treatment was replaced with air containing 0.01% of steam.

| Catalyst No. | Methacrolein conversion (%) | Methacrylic acid selectivity (%) |
|---|---|---|
| (1) | 86.3 | 67.6 |
| (2) | 82.7 | 72.3 |
| (3) | 77.9 | 74.1 |
| (4) | 73.3 | 71.4 |
| (5) | 76.5 | 68.0 |

Comparative Example 4

The same procedure in Example 2 was repeated except that the gas used for the heat treatment was replaced with air containing 5.0% of steam.

| Catalyst No. | Methacrolein conversion (%) | Methacrylic acid selectivity (%) |
|---|---|---|
| (1) | 30.2 | 78.7 |
| (2) | 35.2 | 74.0 |
| (3) | 27.3 | 77.7 |
| (4) | 25.4 | 79.1 |
| (5) | 21.1 | 78.8 |

EXAMPLE 3

500 parts of molybdenum trioxide, 63.3 parts of antimony trioxide and 17.4 parts of chromium trioxide were added to 200 parts of pure water. An aqueous solution of a mixture of 17.5 parts of copper nitrate and 29.3 parts of potassium nitrate was added to the mixture, and then 66.7 parts of 85% phosphoric acid were added thereto under stirring. The mixture was maintained at 50° C. with thorough stirring for 3 h. 80 parts of 28% aqueous ammonia were added slowly thereto. After standing for an additional 2 h, the mixture was evaporated in dryness. The resulting cake was dried at 150° C. for 16 h, pulverized and molded.

The moldings were charged in a reaction tube having an inner diameter of 27.5 mm and a length of 3 m. The temperature was elevated to 390° C. at a rate of 65° C./h while 1500 l/h of air containing 0.05% of ammonia and 0.85% of steam was introduced therein. They were maintained at that temperature for 1 h and then heat-treated for an additional 3 h after reversing the flow direction of the gas. The product was taken out and reacted in the same manner as in Example 1 except that the reaction temperature and space velocity were altered to 310° C. and 700 h$^{-1}$, respectively. The reaction results were as shown below:

| Catalyst No. | Methacrolein conversion (%) | Methacrylic acid selectivity (%) |
| --- | --- | --- |
| (1) | 90.3 | 82.2 |
| (2) | 88.1 | 83.5 |
| (3) | 85.6 | 84.0 |
| (4) | 87.7 | 83.0 |
| (5) | 89.7 | 82.4 |

EXAMPLE 4

3,000 parts of ammonium paramolybdate were dissolved in 14,000 parts of pure water at about 70° C. 163 parts of 85% phosphoric acid were added to the solution and the mixture was stirred. Then, 147 parts of 60% aqueous arsenic acid solution were added thereto under stirring. An aqueous solution of a mixture of 34.1 parts of copper nitrate, 43.0 parts of potassium nitrate and 193 parts of cesium nitrate was added to the mixture. 49.6 parts of ammonium metavanadate were added to the solution with stirring. Finally, 41.3 parts of antimony trioxide were added therein. The mixture was evaporated to dryness under stirring. The resulting cake was dried at 130° C. for 16 h and then pulverized. The powder was carried on a globular silica-alumina carrier in an amount of about 30%.

The resulting catalyst was charged in a reaction tube having an inner diameter of 27.5 mm and a length of 3 m. The temperature was elevated to 380° C. at a rate of 25° C./h while 1,000 l/h of air containing 0.8% of steam was introduced therein. The calculation was carried out at 380° C. for 8 h. After cooling, the product was taken out in order and divided in 5 parts. They were classified as catalysts (1), (2), (3), (4) and (5) from the air-feeding side.

Each of the catalysts was charged in a reaction tube having an inner diameter of 16 mm. A gaseous starting material comprising 4.0% of methacrolein, 47.8% of air, 15% of steam and 33.2% (by volume) of nitrogen was fed therein at a space velocity of 600 h⁻¹ while the bath temperature was maintained at 295° C. The results are shown in the following table:

| Catalyst No. | Methacrolein conversion (%) | Methacrylic acid selectivity (%) |
| --- | --- | --- |
| (1) | 96.8 | 87.1 |
| (2) | 96.0 | 88.0 |
| (3) | 95.4 | 88.8 |
| (4) | 94.9 | 89.1 |
| (5) | 94.6 | 89.9 |

Comparative Example 5

The same procedure as in Example 4 was repeated except that the gas fed in the course of the calcination was replaced with air containing 1% of ammonia and 4% of steam. The results are shown in the following table:

| Catalyst No. | Methacrolein conversion (%) | Methacrylic acid selectivity (%) |
| --- | --- | --- |
| (1) | 42.3 | 76.6 |
| (2) | 48.1 | 80.2 |
| (3) | 57.9 | 82.0 |
| (4) | 54.2 | 84.0 |
| (5) | 50.0 | 84.1 |

EXAMPLE 5

500 parts of ammonium paramolybdate were dissolved in 1,000 parts of pure water. 82.8 parts of ammonium metavanadate were added to the solution. An aqueous solution of 47.7 parts of ferric nitrate was added to the solution. Then, an aqueous solution of 21.0 parts of water glass was added thereto, and the mixture was rapidly evaporated to dryness. The resulting cake was dried at 340° C. for 2 h and pulverized. The powder was carried on a silica-alumina carrier in an amount of about 30%.

The resulting catalyst was charged in a reaction tube having an inner diameter of 27.5 mm and a length of 3 m. The temperature was elevated to 370° C. at a rate of 70° C./h while 500 l/h of air containing 0.5% of steam was introduced therein. The heat treatment was carried out at that temperature for 2 h.

The product was taken out and used in the same manner as in Example 1 except that methacrolein was replaced with acrolein and the reaction temperature was altered to 270° C.

| Catalyst No. | Methacrolein conversion (%) | Methacrylic acid selectivity (%) |
| --- | --- | --- |
| (1) | 96.0 | 85.6 |
| (2) | 95.7 | 86.0 |
| (3) | 95.6 | 86.0 |
| (4) | 94.7 | 87.2 |
| (5) | 94.0 | 87.6 |

EXAMPLE 6

3,000 parts of ammonium paramolybdate were dissolved in 12,000 parts of pure water at 60° C. 196 parts of 85% phosphoric acid and 160 parts of 50% aqueous arsenic acid solution were added to the solution. Then, 82.7 parts of ammonium metavanadate were added therein. An aqueous solution of 85.5 parts of copper nitrate and 276 parts of cesium nitrate was added thereto, and the mixture was maintained at 60° C. under stirring for 2 h. 107 parts of tin oxide were added therein, and the resulting slurry was evaporated to dryness. The cake was dried at 130° C. for 16 h, pulverized and molded under pressure.

The resulting moldings were charged in a reaction tube having an inner diameter of 27.5 mm and a length of 6 m. The temperature was elevated to 385° C. at a rate of 30° C./h while 3000 l/h of air containing 1.5% of steam was introduced therein. The calcination was carried out at 385° C. for 10 h. After completion of the calcination the product was cooled and a gaseous starting material comprising 3.5 vol. % of methacrolein, 47.8 vol. % of air and 48.7 vol % of steam was fed therein at a space velocity of 800 h⁻¹ in a direction opposite to the direction of the gas introduced in the calcination step. The reaction temperature was 300° C. Methacrolein conversion was 87.8%, methacrylic acid selectivity was 85.0% and yield of methacrylic acid was 74.6%.

Comparative Example 6 and the Description of the Drawing

The same procedure as in Example 6 was repeated except that the gaseous starting material was fed in the same direction as the flowing gas fed in the calcination step. Methacrolein conversion obtained was 85.0%, methacrylic acid selectivity was 67.7% and one-pass yield of methacrylic acid was 57.5%. The temperature of the catalyst layer was also examined to obtain the results shown in the FIGURE. The ordinates in the FIGURE inducate the temperature. The arrow shows a higher temperature side. The abscissas indicate the longitudinal direction of the catalyst layer charged in the reaction tube. Symbol A indicates the end of the catalyst charged and B indicates the other end. The calcination gas is fed in the direction of A→B. The starting gas is fed also in the direction of A→B. Solid line a represents the temperature of the catalyst layer and solid line b represents the bath temperature of the reactor. It can be seen from the FIGURE that in the reaction manner in Comparative Example 6, the reaction was carried out mainly in the catalyst zone near the inlet for the gaseous starting material and that the catalyst was utilized non-uniformly.

EXAMPLE 7

3,000 parts of ammonium paramolybdate were dissolved in 8,000 parts of pure water heated to 70° C. 133 parts of ammonium metavanadate were added and dissolved therein. 163 parts of 85% phosphoric acid were added thereto. Then, 101 parts of 60% arsenic acid, an aqueous solution of a mixture of 171 parts of copper nitrate and 143 parts of potassium nitrate, and 56.6 parts of titanium dioxide were added thereto successively. The mixture was maintained at 70° C. under stirring for 3 h and then evaporated to dryness. The resulting cake was dried at 130° C. for 16 h, pulverized and molded under pressure.

The resulting moldings were charged in a reaction tube having an inner diameter of 27.5 mm and a length of 6 m. The temperature was elevated to 250° C. at a rate of 15° C./h while 6,000 l/h of dry air was fed therein. They were maintained at that temperature for 2 h. Then the temperature was elevated to 380° C. at a rate of 35° C./h while 2,000 l/h of air containing 0.9% of steam and 0.06% of ammonia were fed therein, and the calcination was carried out at 380° C. for 12 h.

The temperature was lowered to 270° C., then elevated again slowly to 295° C. while a gaseous starting material comprising 3.5 vol. % of methacrolein, 47.8% of air and 48.7 vol. % of steam was fed at a space velocity of 800 h$^{-1}$ in a direction opposite to that of the gas flow fed in the calcination step. Methacrolein conversion was 86.7%, methacrylic acid selectivity was 82.8% and yield of methacrylic acid was 71.8%. The reaction was further continued for 720 h to obtain methacrolein conversion of 85.2%, methacrylic acid selectivity of 84.1% and yield thereof of 71.6%.

EXAMPLE 8

3,000 parts of ammonium paramolybdate were dissolved in 8,000 parts of pure water heated to 70° C. Then, 163 parts of 85% phosphoric acid were added thereto and, thereafter, 167 parts of 60% aqueous arsenic acid solution were added to the mixture. An aqueous solution of a mixture of 68.4 parts of copper nitrate, 113 parts of thallium nitrate, 71.6 parts of potassium nitrate and 82.8 parts of cesium nitrate was added thereto. 33.1 parts of ammonium metavanadate and then 41.3 parts of antimony trioxide were added therein, and the mixture was evaporated under stirring to dryness.

The resulting cake was pulverized and carried on a silica-alumina carrier. The catalyst thus obtained was charged in a reaction tube having a length of 3 m. The temperature was elevated to 380° C. at a rate of 25° C./h while 1500 l/h of air containing 0.5% of steam was fed therein, and the calcination was effected at 380° C. for 10 h. The reaction was carried out in the same manner as in Example 7 except that the reaction temperature was altered to 320° C. to obtain methacrolein conversion of 92.0%, methacrylic acid selectivity of 86.0% and yield of methacrylic acid of 79.1%.

EXAMPLE 9

500 parts of ammonium paramolybdate were dissolved in 1,000 parts of pure water. 66.2 parts of ammonium metavanadate were added and dissolved therein. An aqueous solution of 95.4 parts of ferric nitrate was added thereto. Further, 33.6 parts of water glass were added to the mixture. The mixture was evaporated under stirring to dryness and then dried at 340° C. for 2 h. The resulting cake was thoroughly pulverized and carried on a silica-alumina carrier.

The catalyst thus obtained was charged in a reaction tube having an inner diameter of 27.5 mm and a length of 3 m. The temperature was elevated to 360° C. at a rate of 60° C./h while 300 l/h of air containing 0.08% of steam was introduced therein and the mixture was maintained at that point for 2 h.

The reaction was carried out in the same manner as in Example 6 except that methacrolein was replaced with acrolein and the reaction temperature and space velocity were altered to 265° C. and 500 h$^{-1}$, respectively. Acrolein conversion of 93.9%, acrylic acid selectivity of 86.0% and yield of acrylic acid of 80.8% were obtained.

As shown by these examples, the process of the present invention for the calcination of the catalyst allows a large amount of the catalyst to be calcined uniformly. Particularly when the calcination is effected in a reaction tube, the gaseous starting material can be fed therein after the calcination, whereby an unsaturated carboxylic acid can be produced in a high yield. This is a quite advantageous process from the industrial viewpoint.

The invention now being fully described, it will be apparent to one of ordinary skill in the art that many changes and modifications can be made thereto without departing from the spirit or scope of the invention as set forth herein.

What is claimed as new and desired to be secured by Letters Patent of the United States is:

1. A process for improving the operating characteristics of a phosphorous-, molybdenum-, and oxygen-containing catalyst used for the production of an unsaturated carboxylic acid by gas phase catalytic oxidation of a corresponding unsaturated aldehyde, comprising the step of:

calcinating said catalyst at a temperature of 300°-500° C. while a gas containing 0.05-3 vol. % of ammonia and/or steam is passed over said catalyst prior to using said catalyst for the production of said acid.

2. The process of claim 1, wherein the gas is a molecular oxygen-containing gas.

3. The process of claim 1, wherein the calcinating is effected in a reaction tube later used for the gas phase catalytic oxidation of an unsaturated aldehyde.

4. The process of claim 1, wherein the direction of gas flow is reversed in the course of the calcinating.

5. The process of claim 1, wherein the temperature is elevated to the catalyst calcination temperature of 300°-500° C. at a rate of 10°-200° C./h.

6. The process of claim 1, wherein the catalyst comprises phosphorous, molybdenum, an alkali metal, oxygen and at least one member selected from the group consisting of arsenic, antimony, bismuth, copper, vanadium, tungsten, iron, manganese, tin, zirconium, cobalt, nickel, zinc, selenium, cadmium, niobium, tantalum, magnesium, silicon, aluminum, titanium, rhodium, cerium, calcium, strontium, barium, germanium, lead, chromium, thallium, indium, palladium, silver, tellurium and ammonium.

7. The process of claim 1, wherein the catalyst comprises phosphorous, molybdenum, thallium, oxygen and at least one member selected from the group consisting of arsenic, antimony, bismuth, copper, vanadium, tungsten, iron, manganese, tin, zirconium, cobalt, nickel, zinc, selenium, cadmium, niobium, tantalum, magnesium, silicon, aluminum, titanium, rhodium, cerium, calcium, strontium, barium, germanium, lead, chromium, indium, palladium, silver, tellurium and ammonium.

* * * * *